(12) United States Patent
Kato et al.

(10) Patent No.: US 11,332,737 B2
(45) Date of Patent: *May 17, 2022

(54) METHOD FOR COUNTING NUMBER OF NUCLEIC ACID MOLECULES

(71) Applicants: DNA Chip Research Inc., Tokyo (JP); Osaka Prefectural Hospital Organization, Osaka (JP)

(72) Inventors: Kikuya Kato, Osaka (JP); Yoji Kukita, Osaka (JP); Ryo Matoba, Tokyo (JP)

(73) Assignees: DNA CHIP RESEARCH INC., Tokyo (JP); OSAKA PREFECTURAL HOSPITAL ORGANIZATION, Osaka (JP)

( * ) Notice: Subject to any disclaimer, the term of this patent is extended or adjusted under 35 U.S.C. 154(b) by 164 days.

This patent is subject to a terminal disclaimer.

(21) Appl. No.: 16/773,570

(22) Filed: Jan. 27, 2020

(65) Prior Publication Data
US 2020/0385708 A1  Dec. 10, 2020

Related U.S. Application Data

(62) Division of application No. 15/322,883, filed as application No. PCT/JP2015/069114 on Jul. 2, 2015, now Pat. No. 10,584,331.

(60) Provisional application No. 62/020,210, filed on Jul. 2, 2014.

(51) Int. Cl.
| | | |
|---|---|---|
| *C12Q 1/68* | (2018.01) | |
| *C12Q 1/6874* | (2018.01) | |
| *G16B 45/00* | (2019.01) | |
| *C12N 15/10* | (2006.01) | |
| *C12N 15/00* | (2006.01) | |

(52) U.S. Cl.
CPC ......... *C12N 15/1065* (2013.01); *C12N 15/00* (2013.01); *C12Q 1/68* (2013.01); *C12Q 1/6874* (2013.01); *G16B 45/00* (2019.02)

(58) Field of Classification Search
CPC .... C12N 15/00; C12N 15/1065; G18B 45/00; C12Q 1/68; C12Q 1/6874; C12Q 1/6869; C12Q 2525/155; C12Q 2525/179; C12Q 2525/191; C12Q 2563/179
See application file for complete search history.

(56) References Cited

U.S. PATENT DOCUMENTS

| | | | |
|---|---|---|---|
| 9,315,857 B2 * | 4/2016 | Fu | C12Q 1/6837 |
| 10,287,630 B2 * | 5/2019 | Xie | C12N 15/1065 |
| 10,584,331 B2 * | 3/2020 | Kato | C12N 15/00 |
| 2013/0053256 A1 | 2/2013 | Hubbell | |

FOREIGN PATENT DOCUMENTS

WO  2013033721 A1  3/2013

OTHER PUBLICATIONS

V.R. Akmaev et al.: Correction of Sequence-based artifacts in serial analysis of gene expression, Bioinformatics, vol. 20, No. 8, Feb. 10, 2004 (Feb. 10, 2004), pp. 1254-1263, XP055428075, GB ISSN: 1367-4803, DOI: 10.1093/bioinformatics/bth077*abstract, Fig. 1, p. 1348 col. 1 para. 2 and 3 and Fig. S1 (supplementary information).
Supplementary European Search Report of EP15815855.0 (PCT/JP2015/069114) dated Dec. 12, 2017.
Casbon et al., A method for counting PCR template molecules with application to next-generation sequencing. Nucleic Acids Res., vol. 39, e81 (2011).
Kinde et al., Detection and quantification of rare mutations with massively parallel sequencing. Proc. Natl. Acad. Sci. USA, vol. 108, pp. 9530-9535 (2011).
Schmitt et al., Detection of ultra-rare mutations by next-generation sequencing. Proc. Natl. Acad. Sci. USA, vol. 109, No. 36, pp. 14508-14513 (2012).
Shiroguchi et al., "Digital RNA sequencing minimizes sequence-dependent bias and amplification noise with optimized single-molecule barcodes", Proc. Natl. Acad. Sci. USA, vol. 109, No. 4, pp. 1347-1352 (2012).
Kukita et al., High-fidelity target sequencing of individual molecules identified using barcode sequences: de novo detection and absolute quantitation of mutations in plasma cell-free DNA from cancer patients, DNA Res., EPub, vol. 22, No. 4, pp. 269-277 (2015).

* cited by examiner

*Primary Examiner* — David C Thomas
(74) *Attorney, Agent, or Firm* — Troutman Pepper Hamilton Sanders LLP

(57) ABSTRACT

The object of the invention is to provide a method for counting the number of nucleic acid molecules in a mixture of a plurality of nucleic acid molecules more highly accurately. This is a method for highly accurately counting the number of nucleic acid molecules by detecting the read errors that occur when determining a nucleic acid base sequence, wherein the method has: a step for adding a barcode-sequence-generating oligonucleotide to a mixture of a plurality of nucleic acid molecules, thereby linking barcode sequences unique to the nucleic acid molecules to the base sequences constituting each of the nucleic acid molecules; a step for determining the base sequences of the nucleic acid molecules to which the barcode sequences have been linked; a step for detecting read errors in the barcode sequences for which the base sequences have been determined; and a step for calculating the proportion of barcode sequences free of read errors to all of the barcode sequences for which the base sequences have been determined, on the basis of the number of reads of the barcode sequences for which the base sequences have been determined, the above-mentioned barcode-sequence-generating oligonucleotide comprising a maximum of five bases, and the number of barcode sequences free of read errors indicating the number of nucleic acid molecules in the mixture.

17 Claims, 6 Drawing Sheets

Specification includes a Sequence Listing.

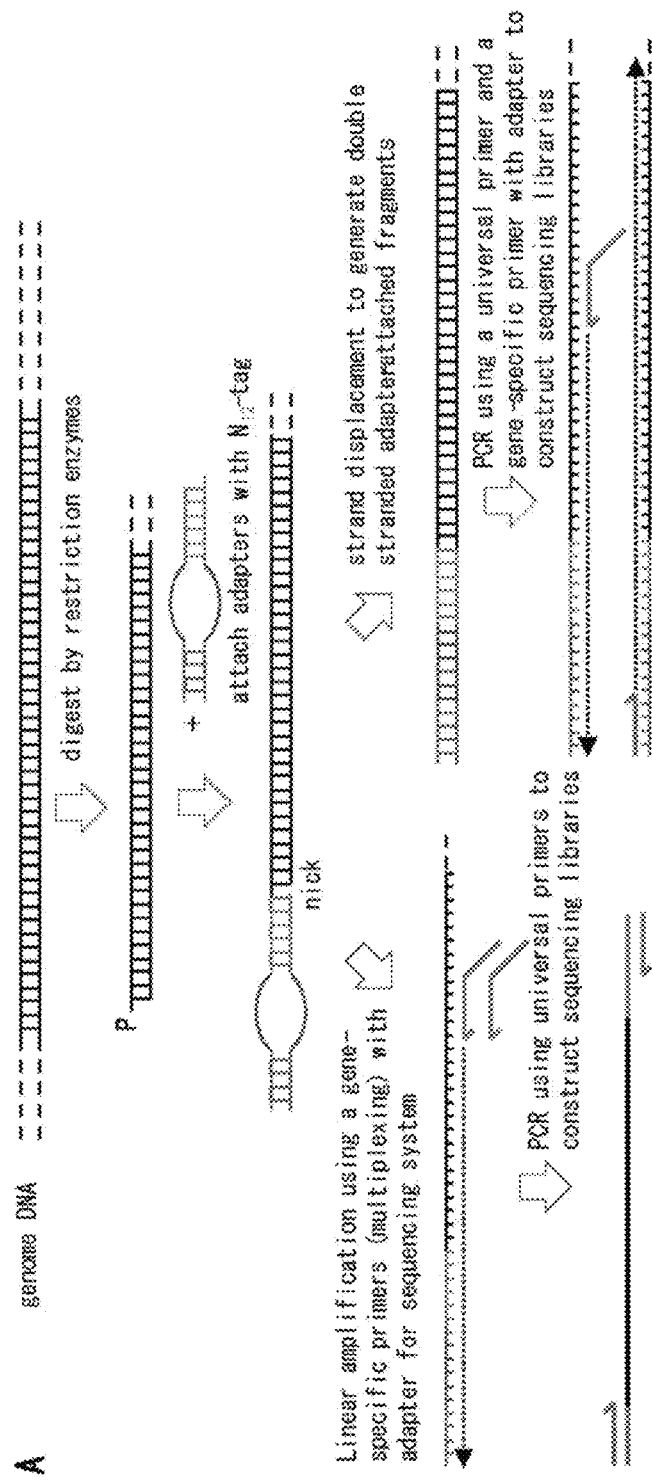
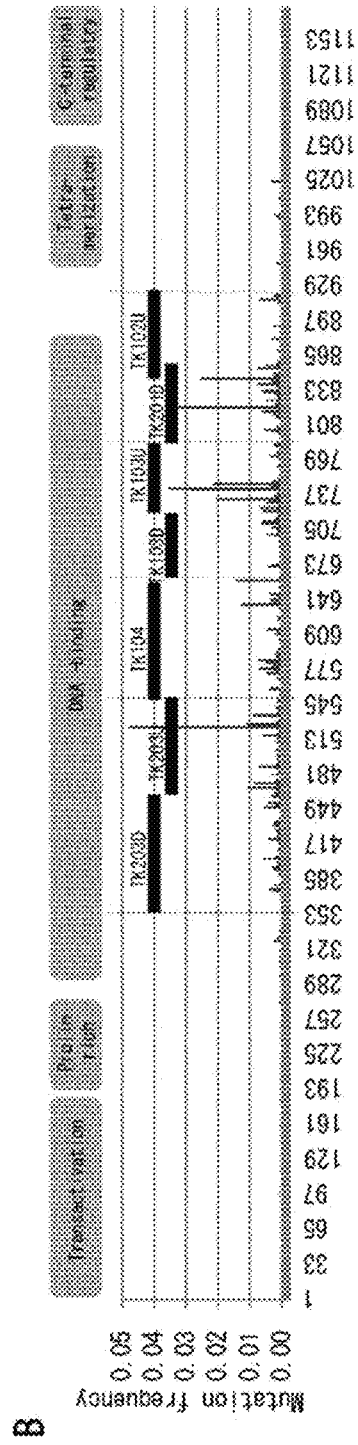
FIG. 1A
FIG. 1B

SEQUENCE LISTING

```
<160> NUMBER OF SEQ ID NOS: 6

<210> SEQ ID NO 1
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: N
<222> LOCATION: (1)..(13)
<223> OTHER INFORMATION: a mixture of A, T, G, C
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 1
nacntngana gtn                                                    13

<210> SEQ ID NO 2
<211> LENGTH: 15
<212> TYPE: DNA
<213> ORGANISM: Artificial Sequence
<220> FEATURE:
<223> OTHER INFORMATION: Synthetic sequence
<220> FEATURE:
<221> NAME/KEY: D
<222> LOCATION: (1)..(15)
<223> OTHER INFORMATION: A, G or T
<220> FEATURE:
<221> NAME/KEY: H
<222> LOCATION: (1)..(15)
<223> OTHER INFORMATION: A, T or C
<220> FEATURE:
<221> NAME/KEY: V
<222> LOCATION: (1)..(15)
<223> OTHER INFORMATION: A, G or C
<220> FEATURE:
<221> NAME/KEY: B
<222> LOCATION: (1)..(15)
```

```
<223> OTHER INFORMATION: G, T or C

<400> SEQUENCE: 2
dhvbdhvbdh vbdhv                                                    15

<210> SEQ ID NO 3
<211> LENGTH: 11
<212> TYPE: DNA
<213> ORGANISM: Artificial Sequence
<220> FEATURE:
<223> OTHER INFORMATION: Synthetic sequence

<400> SEQUENCE: 3
tgcatgatac g                                                        11

<210> SEQ ID NO 4
<211> LENGTH: 13
<212> TYPE: DNA
<213> ORGANISM: Artificial Sequence
<220> FEATURE:
<223> OTHER INFORMATION: Synthetic sequence

<400> SEQUENCE: 4
tgcatggatt acg                                                      13

<210> SEQ ID NO 5
<211> LENGTH: 12
<212> TYPE: DNA
<213> ORGANISM: Artificial Sequence
<220> FEATURE:
<223> OTHER INFORMATION: Synthetic sequence

<400> SEQUENCE: 5
tgcatgatta cg                                                       12

<210> SEQ ID NO 6
<211> LENGTH: 15
<212> TYPE: DNA
<213> ORGANISM: Artificial Sequence
<220> FEATURE:
<223> OTHER INFORMATION: Synthetic sequence
<220> FEATURE:
<221> NAME/KEY: B
<222> LOCATION: (1)..(15)
<223> OTHER INFORMATION: G, T or C
<220> FEATURE:
<221> NAME/KEY: D
<222> LOCATION: (1)..(15)
<223> OTHER INFORMATION: A, G or T
<220> FEATURE:
<221> NAME/KEY: H
<222> LOCATION: (1)..(15)
<223> OTHER INFORMATION: A, T or C
<220> FEATURE:
<221> NAME/KEY: V
<222> LOCATION: (1)..(15)
<223> OTHER INFORMATION: A, G or C

<400> SEQUENCE: 6
bdhvbdhvbd hvbdh                                                    15
```

METHOD FOR COUNTING NUMBER OF NUCLEIC ACID MOLECULES

FIELD OF THE INVENTION

The present invention relates to a method for counting the number of nucleic acid molecules in a nucleic acid molecule mixture. Particularly, the present invention relates to a method for counting the number of nucleic acid molecules highly accurately by adding a sequence for identifying each molecule to nucleic acid base sequences in a mixture of a plurality of nucleic acid molecules so as to detect read errors within identified sequences that occur when sequencing.

BACKGROUND OF THE INVENTION

As a technique for obtaining information about tumor in the body by sampling blood, circulating tumor DNA (ctDNA), which is cell free DNA (cfDNA) released in blood from a dead cancer cell, has recently been used. This ctDNA is believed to be a carrier for transferring genetic information about solid tumor to a peripheral blood vessel, and it is expected that the use of ctDNA facilitates analyses of hereditary tumor heterogeneity (e.g., cancer cell evolution caused by the disease course). The size of cfDNA is 170 base pairs on average and its half-life is 16.5 minutes. One to several thousand genomic ctDNAs are contained in one milliliter of blood.

A wide variety of techniques have been developed for detecting this ctDNA, while digital PCR and its related techniques, particularly massively parallel DNA sequencers, so-called next-generation sequencers, are leading techniques. However, the disadvantage of such next-generation sequencers is read errors that frequently occur, and the number of erroneous constants and false positive increases, as the number of regions for which base sequences should be determined increases. Another disadvantage is that there is a step for amplifying the entire DNA to be analyzed at a template preparation stage for massively parallel sequencing, and thereby the final sequence reads do not reflect the first proportion of DNA molecules. The number of reads normally exceeds the number of DNA molecules to be analyzed, which in turn influences the measurement of alleles in mutations.

A technique used for solving the abovementioned advantages is a barcode sequence (Casbon, J. A., Osborne, R. J., Brenner, S. and Lichtenstein, C. P. 2011, A method for counting PCR template molecules with application to next-generation sequencing. Nucleic Acids Res., 39, e81. Kinde, I., Wu, J., Papadopoulos, N., Kinzler, K. W. and Vogelstein, B. 2011, Detection and quantification of rare mutations with massively parallel sequencing. Proc. Natl. Acad. Sci. USA, 108, 9530-9535). This method enables to label DNA fragments with a random sequence having 10-15 bases in many cases, distinguish reads originated from individual molecules and then group reads originated from each molecule. In other words, DNA sequencing of high quality can be provided by making a consensus of reads, so that the number of sequenced molecules can be counted.

SUMMARY OF THE INVENTION

However, this technique using a barcode sequence also has disadvantages, and one major disadvantage is a read error that occurs in a barcode sequence itself. In other words, this disadvantage affects the basic principle that each molecule is labeled with a single specific barcode. Therefore, an attempt at detecting and removing errors has been made by designing a small group of barcode sequences; however, this approach cannot handle a large number of sequences because each barcode sequence needs to be produced individually. Accordingly, there is a need to develop a method for counting the number of molecules in a mixture of a plurality of nucleic acid molecules highly accurately.

This invention has been made in view of the abovementioned circumstances, and the object of this invention is to provide a method for counting the number of nucleic acids highly accurately by detecting read errors that occur at the time of determining nucleic acid base sequences.

In order to solve the abovementioned problems, the present inventors paid attention to the characteristics of read errors that occur at the time of determining the base sequences of nucleic acid molecules and found that main read errors varied depending on the type of sequencers. After conducting extensive studies, the present inventors found that the proportion of no error can be calculated for each number of reads by designing an appropriate barcode sequence for each characteristic of a read error and analyzing the barcode sequence, and thereby that read errors could appropriately be removed.

More specifically, according to a first major viewpoint of this invention, provided is a method for highly accurately counting the number of nucleic acid molecules by detecting the read errors that occur when determining a nucleic acid base sequence, the method comprising: a step for adding a barcode-sequence-generating oligonucleotide to a mixture of a plurality of nucleic acid molecules, thereby linking barcode sequences unique to the nucleic acid molecules to the base sequences constituting each of the nucleic acid molecules; a step for determining the base sequences of the nucleic acid molecules to which the barcode sequences have been linked; a step for detecting read errors in the barcode sequences for which base sequences have been determined; and a step for calculating the proportion of barcode sequences free of read errors to all of the barcode sequences for which the base sequences have been determined, on the basis of the number of barcode sequences for which the base sequences have been determined, wherein the barcode-sequence-generating oligonucleotide comprises a maximum of five bases, and the number of barcode sequences free of read errors indicates the number of nucleic acid molecules in the mixture.

Such a configuration makes it possible to remove read errors in barcode sequences for which base sequences have been determined; therefore the major premise that one barcode sequence is bound to one nucleic acid molecule can be guaranteed, and the number of nucleic acid molecules in a mixture of nucleic acid molecules prior to the determination of base sequences can accurately be counted.

Moreover, such a configuration also makes it possible to assume with high probability that all of a plurality of base sequences to which a specific barcode sequence is linked have the same sequence, so that the precision of base sequence determination can be enhanced.

Moreover, according to one embodiment of this invention, provided is the abovementioned method, further comprising a step for plotting the abovementioned calculated proportion for each number of reads of the abovementioned barcode sequences for which base sequences have been determined.

Moreover, in this case, according to another embodiment of this invention, provided is the abovementioned method, further comprising a step for removing barcode sequences having the number of reads equal to or less than a prescribed threshold value, on the basis of a graph obtained by the abovementioned plotting step.

Furthermore, according to another embodiment of this invention, the abovementioned detection step can be performed by analyzing the base length or base sequence of each barcode sequence for which base sequence has been determined Moreover, according to another embodiment of this invention, the length of the abovementioned barcode-sequence-generating oligonucleotide may be 5-20 bases or can be set to 12 bases.

Moreover, according to another embodiment of this invention, the abovementioned barcode-sequence-generating oligonucleotide comprises one or more other base sequences in the sequence thereof.

Moreover, according to another embodiment of this invention, a base in the abovementioned barcode-sequence-generating oligonucleotide can be selected from two or three kinds of bases independently for each base site. Moreover, in this case, the abovementioned detection step can be performed by detecting a base that does not constitute the barcode sequence for which base sequence has been determined for each base site of the abovementioned barcode sequence.

Moreover, according to another embodiment of this invention, the abovementioned barcode sequence can be linked to a base sequence constituting the abovementioned nucleic acid molecule by adding an adaptor comprising the abovementioned barcode-sequence-generating oligonucleotide to the base sequence constituting the abovementioned nucleic acid molecule and then amplifying the nucleic acid molecule added with the abovementioned adaptor, using an adaptor primer on the outer side of the barcode-sequence-generating oligonucleotide and a primer specific to the base sequence constituting the abovementioned nucleic acid molecule.

Moreover, according to another embodiment of this invention, the base sequence constituting the abovementioned nucleic acid molecule or an adaptor having the base sequence constituting the abovementioned nucleic acid molecule may comprise a sticky end or a blunt end.

Moreover, according to another embodiment of this invention, the abovementioned read error may be an insertion or deletion of a base sequence, or a base substitution.

Moreover, according to another embodiment of this invention, provided is the abovementioned method, further comprising: a step for determining a consensus sequence of nucleic acid molecules having the same barcode sequence, on the basis of the barcode sequence for which base sequence has been determined; a step for detecting read errors in the base sequences of the nucleic acid molecules for which the base sequences have been determined, on the basis of the consensus sequence; and a step for removing nucleic acid molecules having the read errors.

Moreover, in this case, provided is the method that further comprises a step for counting the number of nucleic acid molecules having mutations by detecting mutations in the base sequences of nucleic acid molecules for which the base sequences have been determined, on the basis of the abovementioned consensus sequence.

Furthermore, according to a second major viewpoint of this invention, provided is a barcode-sequence-generating oligonucleotide to be used in the abovementioned method, wherein a base in the barcode-sequence-generating oligonucleotide is selected from two or three kinds of bases independently for each base site.

According to one embodiment of this invention, the abovementioned barcode-sequence-generating oligonucleotide can comprise one or more other base sequences in the sequence thereof.

The features and marked operation and effects of this invention other than those described above will be made evident for those skilled in the art by referring to the detailed description of the invention and drawings as shown below.

BRIEF DESCRIPTION OF THE DRAWINGS

FIG. 1A is a schematic view showing the construction of libraries of barcode sequences according to one embodiment of this invention.

FIG. 1B is a schematic view showing target regions of human TP53. The cDNA structure in the coding region of the human TP53 gene is shown with a bar graph of a mutation distribution, as seen in COSMIC v63 (http://cancer.sanger.ac.uk/). Vertical dotted lines show boundaries of exons in DNA binding domains. Horizontal black bold lines show target regions used in one embodiment of the present invention.

DETAILED DESCRIPTION OF THE INVENTION

Figure 2A:
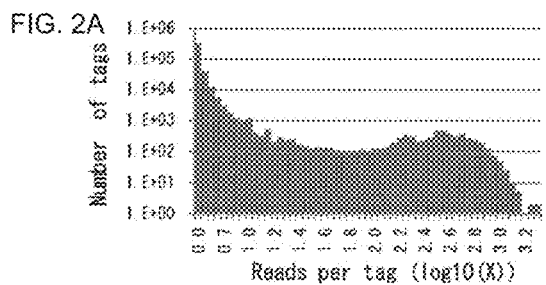
FIG. 2A is a graph showing a distribution of the number of reads per barcode tag. The vertical axis shows the number of different barcode tags, and the horizontal axis shows the number of reads per barcode tag as shown in common logarithms.

A description of one embodiment and examples according to the present invention is given below with reference to drawings.

As described above, the method according to this embodiment for highly accurately counting the number of nucleic acid molecules by detecting the read errors that occur when determining a nucleic acid base sequence comprises: a step for adding a barcode-sequence-generating oligonucleotide to a mixture of a plurality of nucleic acid molecules, thereby linking barcode sequences unique to the nucleic acid molecules to the base sequences constituting each of the nucleic acid molecules; a step for determining the base sequences of the nucleic acid molecules to which the barcode sequences have been linked; a step for detecting read errors in the barcode sequences for which base sequences have been determined; and a step for calculating the proportion of barcode sequences free of read errors to all of the barcode sequences for which the base sequences have been determined, on the basis of the number of barcode sequences for which the base sequences have been determined, wherein the barcode-sequence-generating oligonucleotide comprises a maximum of five bases, and the number of barcode sequences free of read errors indicates the number of nucleic acid molecules in the mixture.

As used herein, the term "read errors" refers to the reading errors that occur when determining a nucleic acid sequence. In the sequencing for detecting mutations and substitutions in specific sequences using a next-generation sequencer, data about sequences, which is called reads obtained as a result of the sequencing, is mapped on a reference sequence that is a known genomic sequence. In this case, reading errors might possibly occur in each read, and it is believed that about 0.1% or more of errors occur relative to the entire base sequence, though it varies depending on next-generation sequencer products and the characteristics of sequences to be read. Moreover, it has been known that the type of read errors that occur frequently or predominantly varies depending on products; base substitution errors are predominant in Illumina products. As used herein, the term "read errors" includes all kinds of the abovementioned errors that occur at the time of sequencing, including, as the type of errors, base insertions, base deletions and base substitutions. Furthermore, read errors may also be caused by PCR errors when preparing templates, though it occur at low frequency.

As used herein, the term "mixture of a plurality of nucleic acid molecules" refers to a mixture of a plurality of DNA molecules or RNA molecules, regardless of the length or sequence of each nucleic acid sequence. Furthermore, a nucleic acid pool originated from a specific tissue or species may also be used.

As used herein, the term "barcode-sequence-generating oligonucleotide" refers to a sequence constituted of a mixture of bases (A, T, G, C, U) that are optional at each base site. Preferably, N (a mixture of A, T, G, C) is used. The length of the base sequence is not particularly limited as long as it is identifiable as a barcode sequence, as described below; preferably, it has 5-20 bases and can appropriately be selected in accordance with each experimental environment such as the type and length of a base sequence to be determined and the origin of a mixture of nucleic acid molecules (e.g., 5, 6, 7, 8, 9, 10, 11, 12, 13, 14, 15, 16, 17, 18, 19 or 20 bases).

Any base can be inserted into the barcode-sequence-generating oligonucleotide, i.e., it is not necessary for the barcode-sequence-generating oligonucleotide to be a continuous sequence. By way of example, in the case that the length of the barcode-sequence-generating oligonucleotide is five, the sequence could be NACNTNGANAGTN (SEQ ID NO: 1) (the underlined portions constitutes the barcode-sequence-generating oligonucleotide); in this case, even after linking it to one molecule as a barcode sequence unique to the molecule, it is possible to identify the barcode sequence and distinguish it from the others simply by knowing the position of N.

Although bases constituting this barcode-sequence-generating oligonucleotide are of five types (A, T, G, C, U) constituting nucleic acids as a whole, two or three kinds of bases can be selected independently for each base site. By way of example, the following sequence can be used: DHVBDHVBDHVBDHV (SEQ ID NO: 2). Here, D is A, G or T, H is A, T or C, V is A, G or C, and B is G, T or C. In addition to DHVB, R (purine base), Y (pyrimidine base), M (A or C), K (G or T), S (G or C) and W (A or T) may be used as bases constituting the barcode-sequence-generating oligonucleotide. In the case of RNA, U can also be used.

As used herein, the term "barcode sequence" refers to a specific sequence of ATGCU, wherein the abovementioned barcode-sequence-generating oligonucleotide has been bound to a base sequence to be sequenced as a sequence unique to the base sequence.

The technology for identifying each molecule using barcode sequences is referred to as a molecular barcoding technology. This molecular barcoding technology is a technology in which a specific base sequence unique to each molecule is linked before the experimental procedures and particularly before PCR amplification and the determination of base sequences and then molecules are identified after the experimental procedures. This is a method carried out based on the use of a massively parallel (next-generation) sequencer and can be achieved by linking a barcode-sequence-generating oligonucleotide to DNA or RNA before the experimental procedures. By grouping base sequences determined by the molecular barcoding technology for each barcode sequence and thereby making a consensus sequence, errors caused by artifacts during the procedures can be eliminated, and also by counting the number of barcode sequences, the number of DNA molecules or RNA molecules before the experimental procedures can be counted.

A barcode-sequence-generating oligonucleotide can be bound to a base sequence to be sequenced by means of any technique. By way of example, it can be achieved by preparing forward and reverse primers specific to a base sequence to be sequenced, linking a barcode-sequence-generating oligonucleotide to those primers and then amplifying the nucleic acid.

Alternatively, it can also be achieved by adding an adaptor to which a barcode-sequence-generating oligonucleotide has been linked by ligation to an end (including a blunt end and a sticky end) in the vicinity of a domain to be sequenced, which has been cut with a restriction enzyme or DNAase or generated by other physical or biochemical methods. In this case, an adaptor primer on the outer side of the barcode sequence is used for PCR amplification as one primer.

In one embodiment of this invention, the abovementioned read errors can be detected by measuring the length of barcode sequences as well as analyzing bases in the barcode sequences. By way of example, in the case of using an Ion Torrent product as a next-generation sequencer, insertion errors and deletion errors are predominant as read errors, as described above. Accordingly, read errors in the barcode sequences can be detected by measuring the length of the barcode sequences. For example, in the case of using $N_{12}$ as the barcode-sequence-generating oligonucleotide, it can be judged that read errors have occurred, when the length of barcode sequences, which have actually been linked to base sequences to be sequenced, is measured and it is found that the length is other than 12.

Similarly, in the case of using an Illumina product, base substitution errors are predominant. In this case, as described above, errors in barcode sequences can be detected by using a barcode-sequence-generating oligonucleotide having two or three kinds of bases independently at each base site. By way of example, in the case of using DHVBDHVBDHVBDHV (SEQ ID NO: 2) as the barcode-sequence-generating oligonucleotide, it can be judged that a read error has occurred when the first base of a barcode sequence, which has actually been linked to a base sequence to be sequenced, is C, because D at the first base side cannot be C.

Based on previous studies, it is known that the number of erroneous barcode sequences is large when the number of reads of base sequences per barcode sequence is small. Accordingly, erroneous sequences, i.e., sequences that are judged to be apparently different nucleic acid molecules can be excluded by first grouping barcode sequences for each number of reads of base sequences, calculating the ratio of barcode sequences free of read errors, and then collecting groups having values equal to or greater than a prescribed threshold value and excluding the rest.

By way of example, in the case of a sequencer characterized in that insertion errors or deletion errors in base sequences are predominant as the characteristics of errors, errors can be judged by the length of barcode sequences, as described above; therefore barcode sequences are grouped for each number of reads per base sequence, and when the length of a barcode-sequence-generating oligonucleotide is 12, the proportion of base sequences having 12 bases is calculated in the barcode sequences of the grouped number of reads, and then plotting is performed for each number of reads. As a result, barcode sequences having the number of reads equal to or less than a prescribed threshold value can be removed, and thereby the number of barcode sequences free of read errors accurately shows the number of nucleic acid molecules in the original nucleic acid molecule group.

On the other hand, in the case of a sequencer characterized in that base substitution errors are predominant as the characteristics of errors, barcode sequences having a base that does not constitute the barcode-sequence-generating oligonucleotide is first detected at each base position. As a result, erroneous barcode sequences are found, and then barcode sequences are grouped for each number of reads per base sequence to calculate the total number of erroneous barcode sequences in the group. Here, the ratio of the number of barcode sequences having read errors actually detected to the total number of barcode sequences having read errors is $2/3$ when there are two kinds of bases at each base site of the barcode-sequence-generating oligonucleotide and $1/3$ when there are three kinds of bases at each base site of the barcode-sequence-generating oligonucleotide. Accordingly, based on this ratio, the ratio can be calculated for the entire barcode-sequence-generating oligonucleotide. For example, in the case of using DHVBDHVBDHVBDHV (SEQ ID NO: 2) as a barcode-sequence-generating oligonucleotide, the total number of barcode sequences having read errors can be found by multiplying the total number of barcode sequences having a base that should not be found at each base site by three. As a result, the total number of erroneous barcode sequences in the group of each number of reads can be estimated. After estimating the total number of errors in this manner, the proportion of barcode sequences free of errors can be plotted for each number of reads and thereby erroneous barcode sequences can be removed, as described above.

As described above, the read errors that occur when determining a nucleic acid sequence are detected, barcode sequences are grouped by the number of reads per barcode sequence (base sequence), and the proportion of barcode sequences free of read errors to the entire barcode sequences for which the base sequences have been determined is plotted for each number of reads, so that a graph can be made. A prescribed proportion of barcode sequences free of errors is set for each experiment, and the number of reads that matches the proportion is found as a threshold value, so that barcode sequences having the number of reads equal to or less than the threshold value can be removed. Additionally, since the number of barcode sequences free of read errors can accurately be counted, the number of nucleic acid molecules in the original mixture of nucleic acid molecules can accurately be found.

Furthermore, in the present invention, base sequences having read errors can be excluded as described above, and therefore there is a high probability that base sequences having the same barcode sequence are those originated from the same nucleic acid molecule. Accordingly, the accuracy of sequencing can be enhanced by determining a consensus sequence of nucleic acid molecules having the same barcode sequence on the basis of the barcode sequence for which the base sequences have been determined, detecting read errors in the base sequences of the nucleic acid molecule for which the base sequences have been determined, and then excluding the base sequences having those read errors.

Furthermore, by determining a consensus sequence of nucleic acid molecules in this manner, it is possible to detect a change in a base at a specific site in almost all reads. Thus, when the base that has changed at a specific base site is predominant and the changed base is a single base, the change can be regarded as a mutation. Accordingly, it is also possible to count the number of nucleic acid molecules having a mutation by counting the number of groups of barcode sequences linked to the base sequences having a mutation.

EXAMPLES

A description of the present invention is given below in more detail with reference to examples, without limiting the invention to those examples.

(DNA sample) As a DNA sample, we used Megapool Reference male DNA (Kreatech Biotechnology, Inc., Amsterdam, Holland), a DNA pool originated from 100 healthy Caucasian males. Genomic DNAs in white blood cells originated from healthy individuals and MIA PaCa-2 pancreatic cancer cell line having an R280W mutation in the TP53 gene were extracted using a standard phenol/chloroform protocol. Data about patients who had active EGFR mutations in lung cancer tissue was collected from Osaka Medical Center for Cancer and Cardiovascular Diseases, and data about patients with stomach cancer was collected from Osaka University Hospital, and a written informed consent was obtained from all patients who participated in the present experiment. The present experiment was approved by the ethics committees of Osaka Medical Center for Cancer and Cardiovascular Diseases and Osaka University Hospital.

Blood plasma was prepared by centrifuging 4-5 mL of EDTA-treated blood at 800 g at room temperature for 10 minutes, and the plasma was transferred to a new tube to be centrifuged again at 15100 g at room temperature for 10 minutes. After the centrifugation, the supernatant of the plasma was transferred to a new tube. The centrifuged liquid sample was frozen at −80° C. DNA was collected from 1.5-2.0 mL of a liquid sample according to the manufacturer's instructions using a QIAamp circulating nucleic acid kit (Quiagen Inc., Hilden, Germany). The concentration of DNA was determined using a Qubit dsDNA HS Assay Kit (Life Technologies, Inc., California, USA).

(Target regions, adaptors and region-specific primers) In order to analyze genomic regions, we designed adaptors and primers that encode the DNA-binding domain of TP53 as well as the mutation hotspots of KRAS and CTNNB1.

(Construction of libraries by linear amplification of barcode strands) Genomic DNA (5-40 ng) or cell free DNA (about 1 mL of the whole blood) was digested with multiple restriction enzymes (Set1: AlwNI and Alw26I; Set2: EarI and NcoI; SetKC: EarI and NmuCI (FastDigest enzymes, Thermo Scientific, Inc., Massachusetts, USA)). The ligation of adaptors having $N_{12}$ barcode sequence tags was performed using E. coli DNA ligase (Takara Bio, Inc., Shiga, Japan). The ligation product was purified twice with 1.2 times in volume of AmPureXP beads (Beckman Coulter, Inc., California, USA). The purified product was linearly amplified by 10 thermal cycles using a region-specific primer mixture and Q5 Hot Start High-Fidelity DNA polymerase (NEB). The purified linearly amplified product was amplified with a PGM/Proton primer and Platinum Taq High Fidelity (Life Technologies, Inc.). This amplified product was purified using AMPureXP beads or by performing agarose gel electrophoresis with a MinElute Gel Extraction Kit (Qiagen, Inc.).

(Massively parallel sequencing) For the Ion Torrent Sequencing system, sequencing templates (emulsion PCR and beads concentration) were prepared from sequencing libraries in accordance with the manufacturer's instructions using an Ion PI Template OT2 200 Kit v2 or v3 (Life Technologies, Inc.) and an Ion OneTouch system (Ion OneTouch Instrument and Ion OneTouch ES, Life Technologies, Inc.). The templates thus prepared were sequenced using an Ion PI Sequencing 200 Kit v2 or v3 and a Proton Sequencer (Life Technologies, Inc.). Raw signals were converted into base calls using Torrent Suite 4.0 or 4.2 (Life Technologies, Inc.) to extract sequencing reads of FASTQ files. Also, sequencing data of the Illumina system was generated in accordance with manufacturer's instructions using a MiSeq system (Illumina, Inc., California, USA) to extract single-end reads of FASTQ files.

(Data analysis) Reads in FASTQ format were classified using 5 bp indices for individual assignments. Sequences between the 5 bp indices and spacer sequences were set as barcode tags. When the total length of the spacer and the subsequent sequence was larger than 70 bases, reads were aligned to target sequences (spacer+target region) with bwa (version 0.6.2) using the bwa-sw mode for reads having a long alignment length and parameters setting "-b5-q2-r1-z10." Reads having long unmeasured ends (10% or more of the total read length) were discarded.

When we analyzed barcode tags of mapped reads at each target region, we obtained tags that were not 12 bp in length due to insertion errors and deletion errors at the time of sequencing, though 12 bp barcode tags were designed. Tags shorter than 9 bp were discarded. In order to correct the maximum number of reads to a normal value, the 11 bp tags and 13 bp tags that were not 12 bp due to insertion or deletion of a single base were classified together with the corresponding 12 bp tags. By way of example, "TGCAT-GATACG" (SEQ ID NO: 3) and "TGCATGGATTACG" (SEQ ID NO: 4) were classified as the barcode "TGCAT-GATTACG" (SEQ ID NO: 5).

Reads having the same barcode sequences were grouped together, and the barcode tags were assigned as 2-read bins according to the number of reads per tag. Then, the ratio of 12 bp tags in each bin was calculated, and a value (proportion) of each bin was averaged using 11 bins around the abovementioned bin. A minimum bin having a mean proportion of 90% or more was used as a threshold value for removing erroneous barcode tags.

After removing erroneous barcode tags having fewer reads than a threshold value, the reads of tags having the same barcode were combined using samtools (version 0.1.18), and consensus sequences were created using VarScan (v2.2.11). In the case of 50 reads or more, the longest 50 reads were analyzed. When 80% or more of reads had an alternative base at a specific position, we called it a mutant. We converted a set of consensus sequences to a FASTQ file and assigned "57" as a quality score for all bases. We aligned a FASTQ file to the sequences of the abovementioned target regions and processed mapping data thus generated using samtools to obtain the per base coverage (pileup files). Subsequently, we arranged the number of bases for each base position.

The sequence error rate was calculated by dividing the number of sequence bases that did not match the human genomic reference sequence by the number of all sequenced bases in the target regions. When using barcode tags, we analyzed consensus sequences of a plurality of reads originated from individual molecules. Reads before constructing the consensus were used for calculating the error rate of normal base sequences.

(Results) (Target sequencing method for binding barcode sequences by adaptor ligation) Barcode sequences can be attached to genomic DNA and transcriptomes by adaptor ligation. For target and amplicon sequencing, barcode sequences may be embedded in PCR primers.

The binding of an adaptor to a restriction enzyme site and the subsequent PCR amplification with an adaptor primer and a single gene-specific primer is a robust technique applied to genomic DNA and RNA by the present inventors. The present inventors also used this method for target sequencing with barcodes. In this method, restriction enzymes with five-, four- or three-base protruding ends can be used that covered most of the human genome. The present inventors used $E.\ coli$ DNA ligase that enabled the sequence-specific ligation of sticky ends generated by a type IIS restriction enzyme. The adaptor sequence used includes five bases for indexing individuals and $N_{12}$ for indexing molecules (which distinguishes a maximum of $1.7 \times 10^7$ molecules). FIG. 1A shows two types of binding methods. The first method (left route) includes linear amplification of a barcode strand and subsequent PCR amplification. The linear amplification is expected to minimize errors in the first round of PCR. The second method (right route) uses replacement synthesis of the complimentary strand of the added barcode, thereby labelling both strands with the same barcode. For subsequent analyses, the present inventors first used an Ion Proton sequencer to perform the first method. The present inventor selected the DNA-binding domain of TP53 that is covered by seven regions as target regions (FIG. 1B).

Figure 2B:
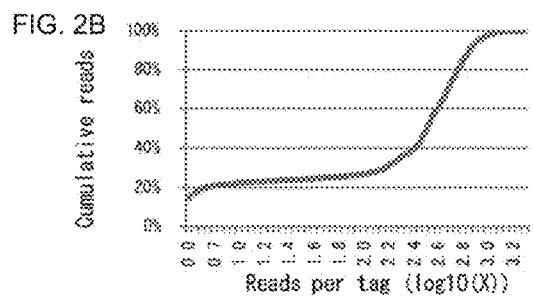
FIG. 2B is a graph showing the number of cumulative reads.

(Monitoring and removal of error barcode tags in the Ion Torrent system) Four out of seven regions of TP53 was sequenced using 5-40 ng of genomic DNA. FIG. 2 shows an example of the relationship between the number of barcode sequence tags and the number of reads grouped by the same barcode sequence tag (reads per tag). In this experiment, the input DNA corresponded to about 10,000 copies of the genome, while the total number of tags was more than 400,000. The majority of these tags had a small number of reads including single reads. However, the corresponding number of reads occupied only a small portion of the total reads obtained (FIG. 2B). This phenomenon was observed in previous studies as well.

Figure 2C:
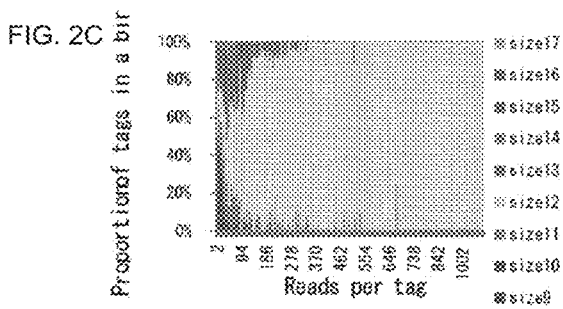
FIG. 2C is a graph showing estimated proportions of erroneous barcode tags and error-free barcode tags to all tags.
Figure 2D:
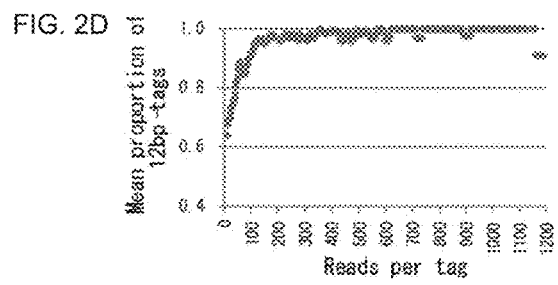
FIG. 2D is a graph showing the mean proportion of 12 bp tags. The 11 bp tags and 13 bp tags, which match the sequence of the 12 bp tag except that there is a single base insertion or deletion relative to the suitable 12 bp tag, are classified together with 12 bp tags. The mean proportion shows a mean proportion of surrounding 11 bins.
Figure 2E:
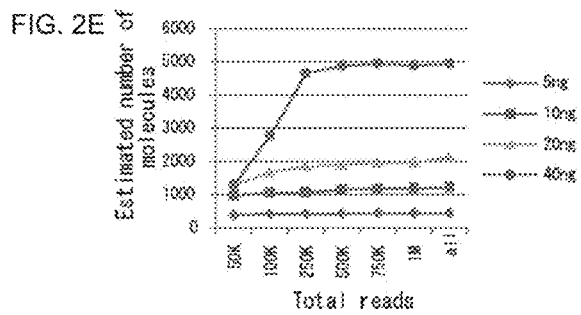
FIG. 2E shows estimated numbers of target molecules after removing erroneous tags. The horizontal axis shows the number of reads used for estimation, and reads are selected from total reads at random (Total number of reads: 5 ng: 1,457,760 reads, 10 ng: 2,251,133 reads, 20 ng: 2,245,038 reads, 40 ng: 2,395,763 reads).
Figure 2F:
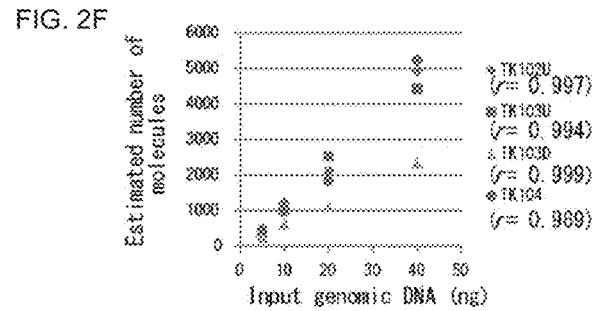
FIG. 2F is a graph showing the correlation between the number of molecules and the amount of input DNA after removing erroneous tags.
Figure 3A:
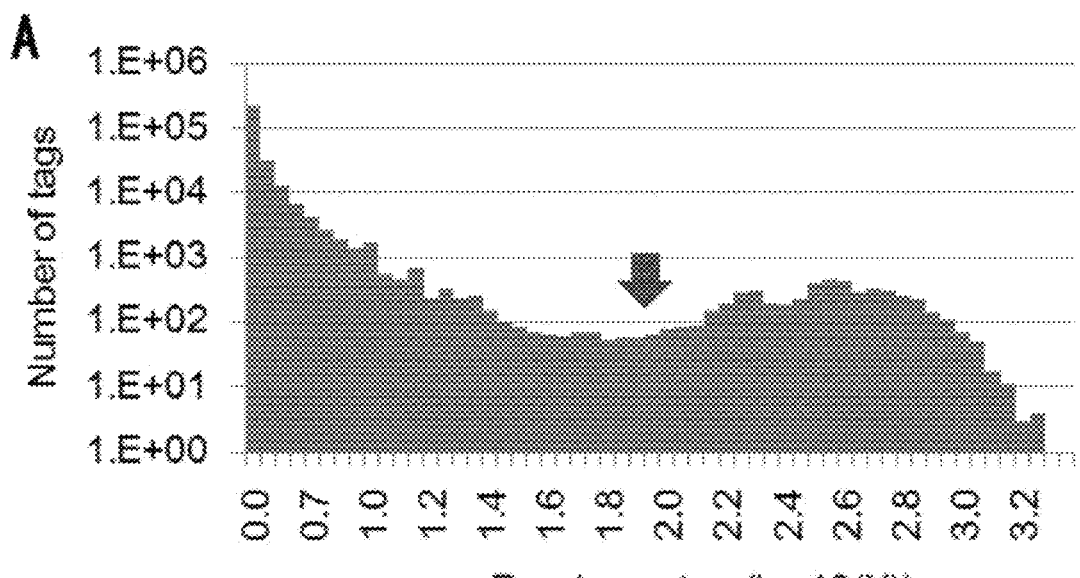
FIG. 3A is a graph showing a distribution of the number of reads per barcode tag. The vertical axis shows the number of different barcode tags, and the horizontal axis shows the number of reads per barcode tag as shown in common logarithms.
Figure 3B:
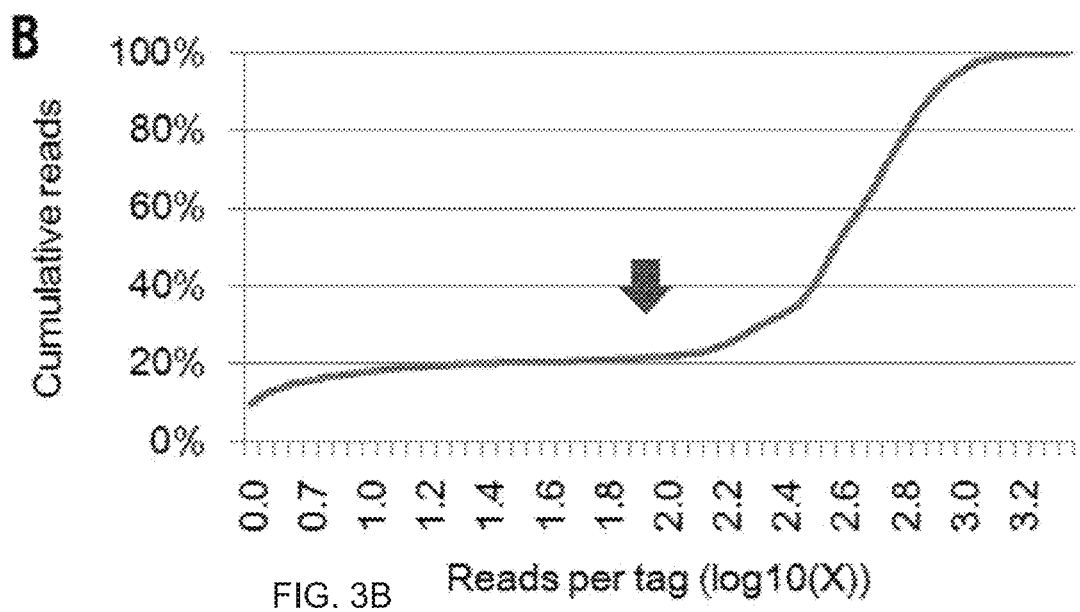
FIG. 3B is a graph showing the number of cumulative reads. An arrow shows a threshold value at the time of removing reads of erroneous tags. The analyzed region was TK102U, and the results were obtained using 40 ng genomic DNA (total number of reads: 2,395,763 reads).

Insertion/deletion errors occupy the majority (more than 90%) of sequencing errors in the Ion Torrent PGM/Proton. Accordingly, the tags generated by read errors can be detected using the tag size. FIG. 2C shows the observed proportions of tags that were classified by size. Non-12 bp tags (i.e., erroneous tags) occupied the majority of tags with small numbers of reads per tag, and the proportion of 12 bp tags gradually increased as the number of reads per tag increased. The abovementioned dynamics suggest that erroneous tags concentrate in small read number fractions and can be removed by setting an appropriate threshold value. In order to improve the utilization rate of reads, the 11 bp and 13 bp tags that matched the sequences of 12 bp tags, with the exception that there was a single inserted or deleted base in the matching 12 bp tags, were grouped together with 12 bp tags. FIG. 2D shows that the proportion of 12 bp tags are plotted against the number of reads. A bin having a minimum value that exceeded 90% in the mean proportion of 12 bp tags in 11 bins therearound was set to a threshold value for removing erroneous tags. The proportion of 12 bp tags obtained exceeded 95% of the corrected proportion, and hardly any improvement was achieved even when more stringent threshold values were set. This threshold value separates two peaks as shown in FIG. 3A. Moreover, the selected threshold value varies depending on various factors including the total number of reads and target regions (11-249 (data points of FIG. 2E) and 57-485 (data points of FIG. 2F)). Through this process, 10-20% of the total reads are discarded (FIG. 3B).

Because the 12-bp tags in the fraction with a small number of reads contained sequences of the original size due to multiple insertion/deletion errors, it was not possible to estimate the number of removed tags free of errors. The right peak in FIG. 2A shows the peak of the distribution of tags free of errors, which means that the fraction corresponding to the tail of the distribution was removed. When M is set as a threshold value, the number of tags free of error between the threshold value and zero does not exceed the number of tags between M and 2M. The estimated maximum number of removed tags free of error, on the basis of the number of 12 bp tags between M and 2M, was 5-10% of the total tags free of errors.

The number of target molecules can be counted using exhaustive sequencing. The number of tags obtained reached saturation at 500,000 reads (FIG. 2E). The correlation between the estimated number of target molecules and the amount of input DNA was observed, and the correlation coefficient was larger than 0.98 (FIG. 2F). Approximately 40% of the input DNA was recovered except for TK103D, while 15% was recovered in TK103D. This calculation was made based on the number of sequenced molecules. The difference in calculation results seems to be caused by the difference in the ligation efficiency at ligation sites.

Conventional studies employ arbitrary standards for removing tags with a small number of reads (e.g., tags with a single read are removed). In the case of removing 1- or 2-read tags, a considerable proportion of erroneous tags remains and the number of tags exceeds the number of target molecules estimated from the amount of input DNA. The number of tags increases with the addition of reads and does not reach saturation, which suggests the generation of new erroneous tags.

Figure 4A:
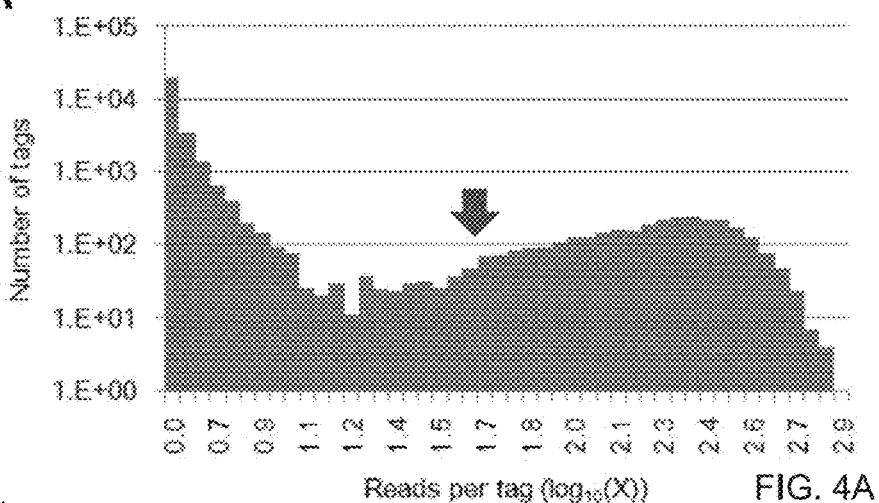
FIG. 4A is a graph showing a distribution of the number of reads per barcode tag. The vertical axis shows the number of different barcode tags, and the horizontal axis shows the number of reads per barcode tag as shown in common logarithms.
Figure 4B:
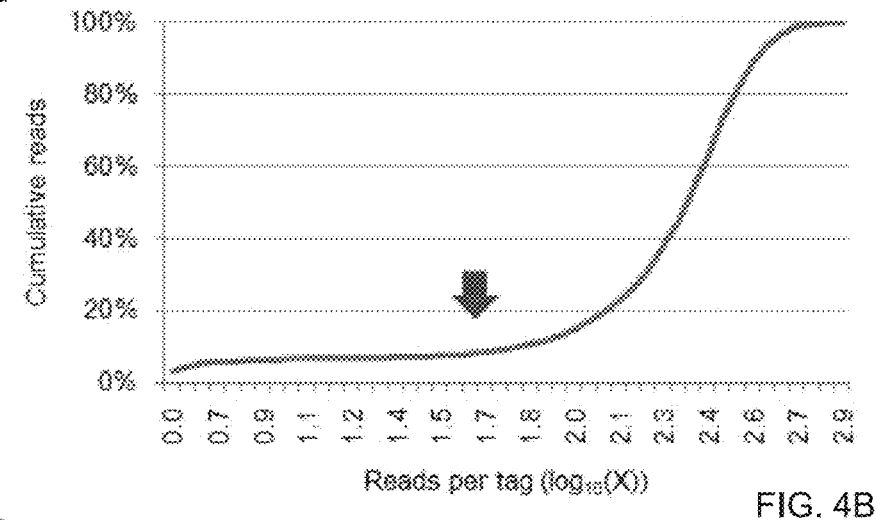
FIG. 4B is a graph showing the number of cumulative reads. An arrow shows a threshold value at the time of removing reads of erroneous tags.
Figure 4C:
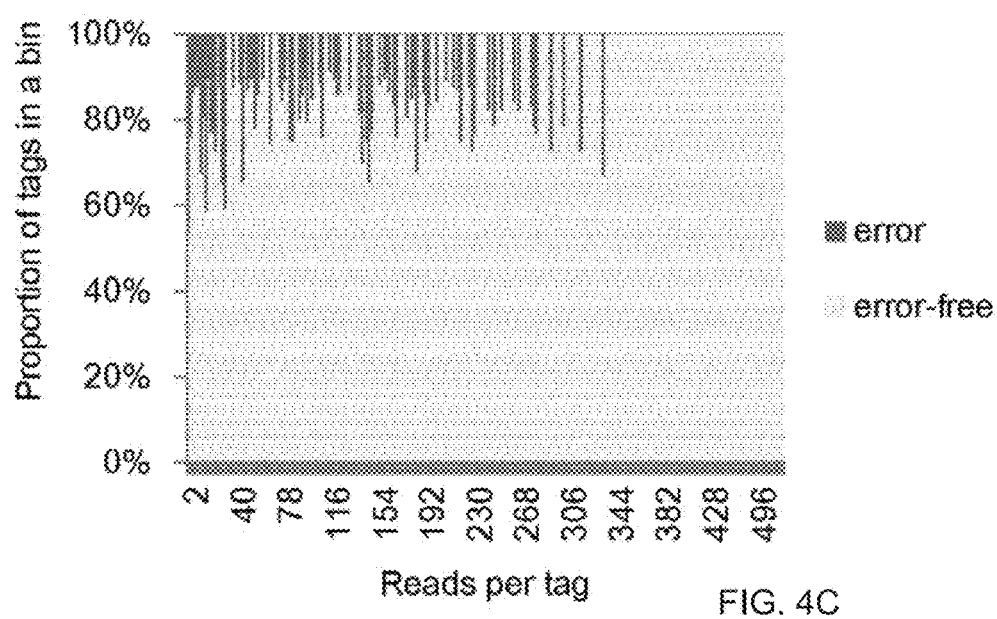
FIG. 4C is a graph showing estimated proportions of erroneous barcode tags and error-free barcode tags to all tags. The analyzed region was TK102U, and the results were obtained using 40 ng genomic DNA (total number of reads: 594,719 reads).
Figure 4D:
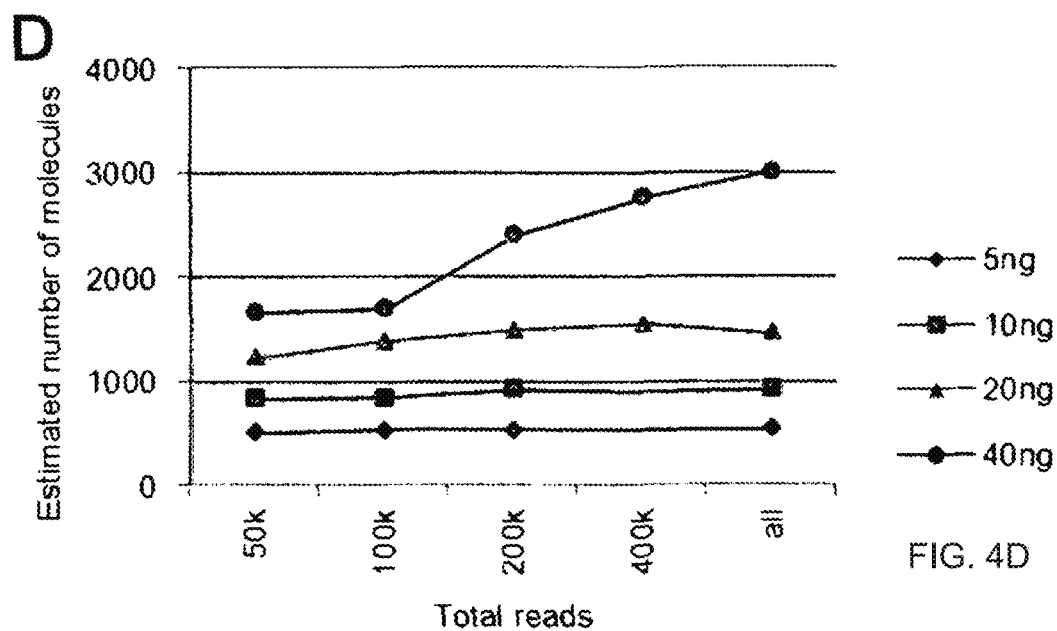
FIG. 4D shows the result when the method according to one embodiment of the present invention was used.
Figure 4E:
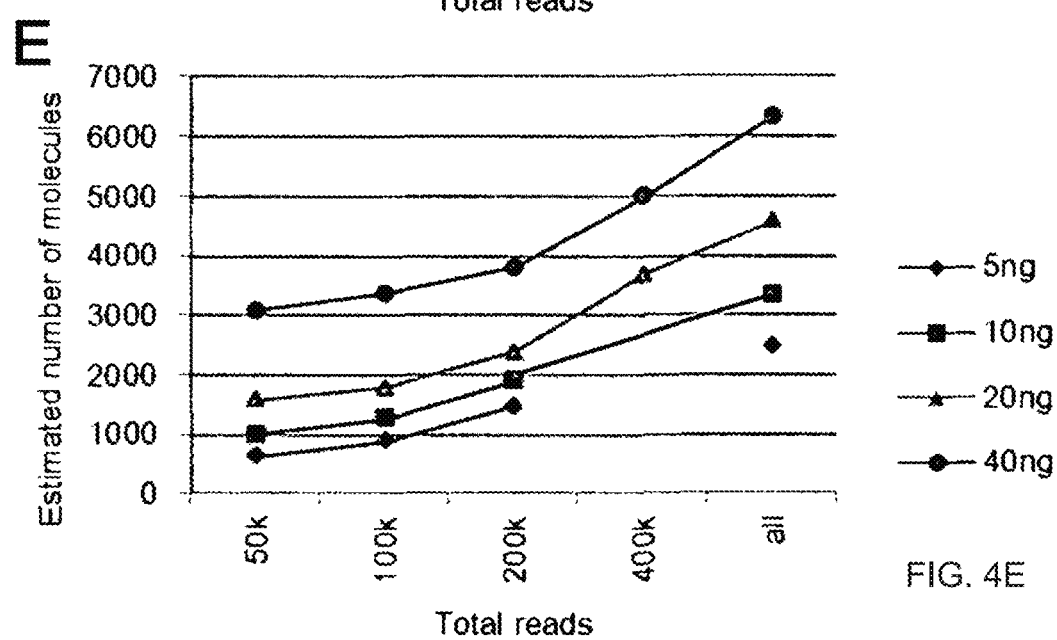
FIG. 4E shows the result when 1- and 2-read tags were removed. Analyses were made using reads selected from total reads at random (total number of reads: 5 ng: 343,932 reads, 10 ng: 404,900 reads, 20 ng: 548,809 reads, 40 ng: 594,719 reads).
Figure 5A:
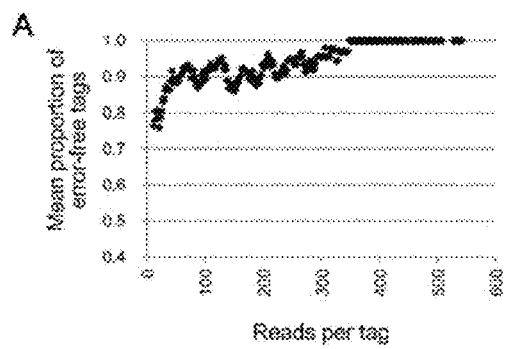
FIG. 5A is a graph showing estimated mean proportions of error-free barcode tags. The mean proportion was calculated in a manner similar to that in FIG. 2D.

(Monitoring and removal of error barcode tags in the Illumina system) The read errors of Illumina sequencers are different from those of Ion Torrent PGM/Proton sequencers; in the case of Illumina, base substitutions mainly cause errors. Nevertheless, the distribution pattern of barcode tags was the same in both sequencing systems (FIG. 4A). In order to accommodate Illumina sequencers, the present inventors used "BDHVBDHVBDHVBDH" (SEQ ID NO: 6) as a barcode for detecting errors. In other words, each base site lacks one of four kinds of bases, and the appearance of a base that should not exist indicates a read error. The total number of erroneous tags can be obtained by multiplying the number of tags having bases that should not exist by three (FIG. 5A, FIG. 4C). Then, a threshold value for removing erroneous tags from the distribution of tags free of errors was determined, as described above. Results obtained using Illumina sequencers were similar to those obtained using Proton sequencers. In other words, 10% of reads were removed (FIG. 4B), and the threshold value varied from 15 to 65 (data points of FIG. 5B). In this case, the number of tags saturated in exhaustive sequencing (FIG. 4D), while it continuously increased with the use of the conventional standard under which 1- or 2-read tags were removed (FIG.

Figure 5B:
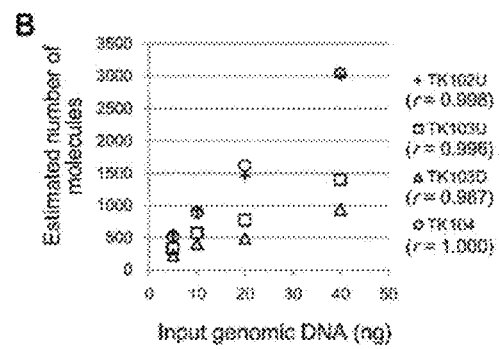
FIG. 5B is a graph showing the correlation between the number of molecules and the amount of input DNA after removing erroneous tags.

4E). The correlation was observed between the estimated number of target molecules and the amount of input DNA (FIG. 5B).

Figure 6:
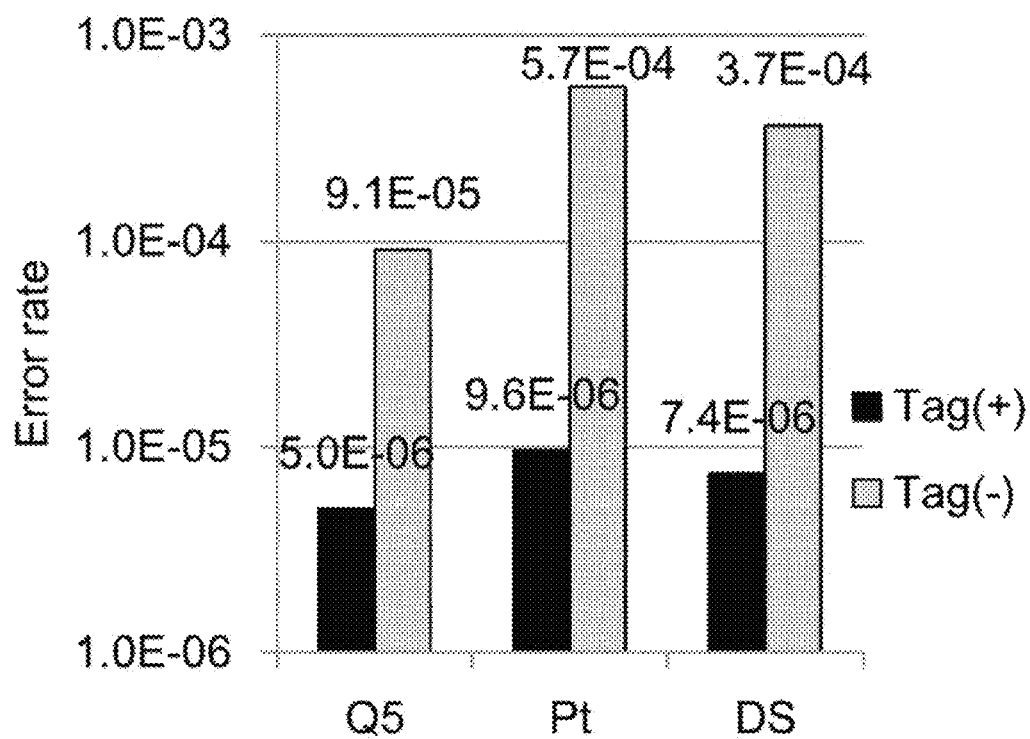
FIG. 6 is a graph showing error rates of sequencing in target regions according to one embodiment of the present invention. Substitution errors when barcode tags were used are shown with black on the left of each column, while substitution errors when barcode tags were not used are shown with gray on the right of each column. Q5 shows a single-strand label after PCR amplification with Q5 DNA polymerase, Pt shows a single-strand label after PCR amplification with a Platinum Taq DNA polymerase High Fidelity kit, and DS shows a double-strand label. The results were obtained using 30 ng genomic DNA. The calculation was based on sequence data obtained from seven (Q5 and Pt) or five (DS exclusive of TK102 and TK103U) regions using an Ion Proton sequencer. The 95% confidence intervals of error rates are as follows: Q5 tag (+): $2.8 \times 10^{-6}$ to $8.8 \times 10^{-6}$, Pt tag (+): $6.9 \times 10^{-6}$ to $1.3 \times 10^{-5}$, DS tag (+): $3.3 \times 10^{-6}$ to $1.6 \times 10^{-5}$, Q5 tag (−): $9.0 \times 10^{-5}$ to $9.3 \times 10^{-5}$, Pt tag (−): $5.7 \times 10^{-4}$ to $5.7 \times 10^{-4}$, DS tag (−): $3.7 \times 10^{-4}$ to $3.7 \times 10^{-4}$.

(Enhanced accuracy by constructing a consensus of reads originated from individual molecules) The use of barcode tags makes it possible to perform highly accurate sequencing by grouping and constructing a consensus of multiple sequences generated from a single molecule. FIG. 6 shows the accuracy of this method. Although two DNA polymerases (Q5 DNA polymerase from NEB and Platinum Taq DNA polymerase High Fidelity from Life Technologies) were compared, no marked difference was observed when barcodes were used (FIG. 6). The second method in which both strands were labelled with the same barcode sequence did not improve the accuracy, as compared with the method in which one strand was labelled (FIG. 6). In the first method, linear amplification cycles were used prior to PCR, and thereby errors can be minimized in the early PCR cycles. Since the first method is simple in terms of experimental procedures, it seems that the first barcode-linking method has an advantage over the second barcode-linking method.

The accuracy of the first barcode-linking method using the Illumina system was $1.8 \times 10^{-6}$ (95% confidence interval, $3.5 \times 10^{-8}$ to $6.9 \times 10^{-6}$).

It goes without saying that the present invention is not limited to the abovementioned one embodiment and can be modified in various manners without departing from the scope and spirit of the invention.

What is claimed is:

1. A method for highly accurately counting the number of nucleic acid molecules by detecting the read errors that occur when determining a nucleic acid base sequence, the method comprising:
   a step for adding a barcode-sequence-generating oligonucleotide to a mixture of a plurality of nucleic acid molecules, thereby linking barcode sequences unique to the nucleic acid molecules to the base sequences constituting each of the nucleic acid molecules;
   a step for determining the base sequences of the nucleic acid molecules to which the barcode sequences have been linked;
   a step for detecting read errors in the barcode sequences for which base sequences have been determined; and
   a step for calculating the proportion of barcode sequences free of read errors to all of the barcode sequences for which the base sequences have been determined, on the basis of the number of reads of barcode sequences for which the base sequences have been determined,
   wherein the barcode-sequence-generating oligonucleotide consists of a maximum of five kinds of bases, and the number of barcode sequences free of read errors indicates the number of nucleic acid molecules in the mixture.

2. The method according to claim 1, further comprising a step for plotting the calculated proportion for each number of reads of the barcode sequences for which base sequences have been determined.

3. The method according to claim 2, further comprising a step for removing barcode sequences having the number of reads equal to or less than a prescribed threshold value, on the basis of a graph obtained by the plotting step.

4. The method according to claim 1, wherein the detection step is performed by analyzing the base length or base sequence of each barcode sequence for which base sequence has been determined.

5. The method according to claim 1, wherein the length of the barcode-sequence-generating oligonucleotide is 5-20 bases.

6. The method according to claim 5, wherein the length of the barcode-sequence-generating oligonucleotide is 12 bases.

7. The method according to claim 1, wherein the barcode-sequence-generating oligonucleotide comprises one or more other base sequences in the sequence thereof.

8. The method according to claim 1, wherein a base in the barcode-sequence-generating oligonucleotide is selected from two or three kinds of bases independently for each base site.

9. The method according to claim 8, wherein the detection step is performed by detecting a base that does not constitute the barcode sequence for each base site of the barcode sequence for which base sequence has been determined.

10. The method according to claim 1, wherein the barcode sequence is linked to a base sequence constituting the nucleic acid molecule by adding an adaptor comprising the barcode-sequence-generating oligonucleotide to the base sequence constituting the nucleic acid molecule and then amplifying the nucleic acid molecule added with the adaptor using an adaptor primer and a primer specific to the base sequence constituting the nucleic acid molecule.

11. The method according to claim 1, wherein the base sequence constituting the nucleic acid molecule comprises a sticky end.

12. The method according to claim 1, wherein the base sequence constituting the nucleic acid molecule comprises a blunt end.

13. The method according to claim 1, wherein the read error is an insertion or deletion of a base sequence, or a base substitution.

14. The method according to claim 1, further comprising:
   a step for determining a consensus sequence of nucleic acid molecules having the same barcode sequence, on the basis of the barcode sequence for which base sequence has been determined;
   a step for detecting read errors in the base sequences of the nucleic acid molecules for which the base sequences have been determined, on the basis of the consensus sequence; and
   a step for removing nucleic acid molecules having the read errors.

15. The method according to claim 14, further comprising a step for counting the number of nucleic acid molecules having mutations by detecting mutations in the base sequences of nucleic acid molecules for which the base sequences have been determined, on the basis of the consensus sequence.

16. The method of claim 1, further comprising a step for selecting a base in the barcode-sequence-generating oligonucleotide from two or three kinds of bases independently for each base site.

17. The method of claim 16, wherein the barcode-sequence-generating oligonucleotide comprises the one or more other base sequences in the sequence thereof.

* * * * *